United States Patent [19]

Borkan et al.

[11] Patent Number: 4,935,243

[45] Date of Patent: Jun. 19, 1990

[54] CHEWABLE, EDIBLE SOFT GELATIN CAPSULE

[75] Inventors: Lionel Borkan, New Vernon; Ira R. Berry, Westfield; Dilip Shah, Flanders, all of N.J.

[73] Assignee: Pharmacaps, Inc., Elizabeth, N.J.

[21] Appl. No.: 286,324

[22] Filed: Dec. 19, 1988

[51] Int. Cl.$^5$ .............................................. A61K 9/28
[52] U.S. Cl. .................................... 424/441; 424/451; 424/452; 424/455; 424/456
[58] Field of Search ............... 424/441, 451, 452, 455, 424/456

[56] References Cited

U.S. PATENT DOCUMENTS

| | | | |
|---|---|---|---|
| 730,926 | 6/1903 | Kobayashi . | |
| 2,580,683 | 1/1952 | Kreuger | 99/165 |
| 3,228,789 | 1/1966 | Glassman | 424/451 |
| 3,515,781 | 6/1970 | Steinberg | 424/37 |
| 3,784,684 | 1/1974 | Bossert et al. | 424/37 |
| 3,851,051 | 11/1974 | Miskel et al. | 424/37 |
| 3,865,603 | 2/1975 | Szymanski | 106/130 |
| 4,279,931 | 7/1981 | Verwaerde et al. | 426/48 |
| 4,346,116 | 8/1982 | Verwaerde et al. | 426/48 |
| 4,486,412 | 12/1984 | Shah et al. | 424/456 |
| 4,532,126 | 7/1985 | Ebert et al. | 424/48 |
| 4,595,583 | 6/1986 | Eckenhoff et al. | 424/438 |
| 4,795,642 | 1/1987 | Cohen et al. | 424/455 |

FOREIGN PATENT DOCUMENTS 5944096  7/1981  Japan .

Primary Examiner—Ellis P. Robinson
Assistant Examiner—P. L. Prater
Attorney, Agent, or Firm—Merchant, Gould, Smith, Edell, Welter & Schmidt

[57] ABSTRACT

In accordance with the present invention, there is provided a chewable, edible soft gelatin capsule which comprises a shell comprising water, gelatin, plasticizer, and an amount of hydrogenated starch hydrolysate effective to render said shell dispersible and soluble in the mouth of the user; and a soft gelatin capsule fill material in which an active ingredient, preferably a biologically-active agent, is dispersed or dissolved.

19 Claims, No Drawings

CHEWABLE, EDIBLE SOFT GELATIN CAPSULE

FIELD OF THE INVENTION

The invention relates to chewable and edible soft gelatin capsules, the shells of which comprise gelatin, water, plasticizer and a hydrogenated starch hydrolysate.

BACKGROUND OF THE INVENTION

Pharmaceutical agents can be encapsulated in either a hard or soft gelatin shell. Hard gelatin capsules are filled with dry materials such as powders or time-release beadlets by introducing the material into one section of the capsule and capping it with a second section. The shell of a hard gelatin capsule is not plasticized, unlike that of a soft gelatin capsule, which is plasticized by the addition of glycerin, sorbitol, or a similar polyol. Instead of dry materials, soft gelatin capsules generally enclose a fluid or semi-fluid fill material or "vehicle" in which the active ingredient is dispersed or dissolved.

Soft gelatin encapsulation of a solution or dispersion of a pharmaceutical agent in a liquid vehicle or carrier offers many advantages over other dosage forms such as compressed, coated or uncoated solid tablets or bulk liquid preparations. Gelatin encapsulation of a solution or dispersion permits accurate delivery of a unit dose, an advantage which becomes especially important when relatively small amounts of the active ingredient must be delivered, as in the case of certain hormones. Such uniformity is more difficult to achieve via a tabletting process wherein solids must be uniformly mixed and compressed, or via incorporation of the total dose of active ingredient into a bulk liquid carrier which must be measured out prior to each oral administration. Soft gelatin capsules are also more easily transported by patients than bulk liquids, since only the required number of doses need be removed from the package.

Soft gelatin encapsulation further provides the potential to improve the bioavailability of pharmaceutical agents. Relatively insoluble active ingredients can be dispersed in a liquid or gelled carrier to provide faster absorption upon rupture of the capsule. For example, Miskel et al. (U.S. Pat. No. 3,851,051) disclose soft gelatin capsules which contain aqueous solutions or suspensions of active ingredients in a water-soluble gel lattice matrix which is formulated to rapidly disperse upon rupture of the capsule shell.

A well-recognized difficulty in the art of soft gelatin encapsulation is that the gelatin capsule shell can be deleteriously effected by water or other aqueous solvents present in the capsule fill material. One way in which previous investigators have addressed the problem of the delivery of an aqueous fill material in a water soluble capsule shell has been by modifying the composition of the shell. For example, the shells of soft gelatin capsules have been modified in order to produce an increased stability of the shell to withstand dissociation by an aqueous capsule fill material. Szymanski et al. (U.S. Pat. No. 3,865,603) disclose gelatin compositions which are "extended" by adding to the gelatin of the shell fluidity starches and thermally modified starches, both of which are chemically modified by the addition of monoreactive moieties.

Kreuger (U.S. Pat. No. 2,580,683) discloses the addition of non-hygroscopic water soluble substances (i.e., substances whose physical characteristics will not be appreciably altered by the effects of water vapor) to the shell of gelatin capsules which have been filled with aqueous solutions of an ingredient compounded with a hygroscopic substance. Sugars are disclosed as the preferred non-hygroscopic constituent of the capsule wall. Raising the sugar content of the capsule wall is disclosed as a means of reducing the required content of dry material in the fill.

Morishita (Japanese Application No. 56-89833) discloses a shell material formed from gelatin, tannic acid, water, and "sugar-type ethyl alcohol, grape sugar, or a similar sugar." Morishita further discloses that this acidic shell encloses a non-acidic filler.

Kobayashi (U.S. Pat. No. 730,926) discloses a soluble, filmy substance used as a wrapper for medicines, either powders or pills, which comprises isinglass or gelatin, starch, and water. A film of "substantially equal parts" of starch and gelatin is disclosed which is made of edible ingredients, and which is soluble in saliva or gastric juice. The film disclosed by Kobayashi is used by wrapping it around medicines, and then putting the wrapped medicine in water, so that the film swells and softens.

The soft gelatin-based compositions commonly employed to form the shells of soft gelatin capsules are not palatable or edible as those terms are understood in the art. Although they are not toxic, most shells yield a gummy, unpleasant tasting, intractable mass in the mouth if they are chewed. However, a gelatin shell which is chewable and edible in the sense that it is pleasant tasting and can be readily fragmented, dissolved, and swallowed would be advantageous for a number of reasons.

For example, in instances where a user is in medical distress from the sudden attack of a condition such as angina pectoris, rapid release of the active ingredient in the fill material of a capsule into the mouth is essential. The shell of a capsule must dissolve rapidly, without leaving any intractable, insoluble residue in the mouth upon which the distressed user might choke. Additionally, when the active ingredients are palatable and thus need not be swallowed whole, soft gelatin capsules provide a convenient delivery vehicle for a unit dosage of the active ingredient. Children and elderly users may not be able to swallow entire capsules, tablets, or pills. Soft gelatin capsules allow these users to easily chew and ingest the active ingredients within the capsules in a palatable form.

Therefore, a need exists for a soft gelatin capsule comprising a shell which is readily chewable and edible.

BRIEF DESCRIPTION OF THE INVENTION

The present invention provides a chewable, edible soft gelatin capsule which comprises:
(a) a soft gelatin shell which comprises about 20–45% gelatin; about 15–30% water; about 17.5–35% plasticizer; and about 5–25% of a hydrogenated starch hydrolysate; and wherein said shell encloses
(b) a soft gelatin capsule fill material.

Preferably the soft gelatin capsule of the invention provides a pharmaceutical unit dosage form of a biologically active substance such as a drug, a mineral, or a vitamin. However, the capsule may also provide a means to deliver a confection, a breath-freshener, or a similar non-toxic ingestible material.

As used herein, the term "soft gelatin capsule fill material" is intended to mean a substantially water-free material (less than or equal to about 5–7% water) which includes at least one active compound and optional amounts of co-solvents, buffers, surfactants, thickeners, and the like. The fill material may be of solid, semi-solid, gel, or liquid form, so long as it is compatible with soft gelatin encapsulation, i.e., it does not substantially degrade the soft gelatin shell.

Unless otherwise indicated, all percentages given herein are percentages by weight of the gelatin shell.

DETAILED DESCRIPTION OF THE INVENTION

In accordance with the present invention, there is provided a chewable, edible soft gelatin capsule which comprises a shell comprising water, gelatin, plasticizer, and an amount of hydrogenated starch hydrolysate effective to render said shell dispersible and soluble in the mouth of the user; and a soft gelatin capsule fill material in which an active ingredient, preferably a biologically-active agent, is dispersed or dissolved.

Soft Gelatin

The starting gelatin material used in the manufacture of capsules is obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Gelatin may also be derived from the skin of cold water fish. Blends of Type A and Type B gelatins can be used to obtain a gelatin with the requisite viscosity and bloom strength characteristics for capsule manufacture. Gelatin can be obtained from the Sigma Chemical Company, St. Louis, Mo. For a general description of gelatin and gelatin-based capsules, see *Remington's Pharmaceutical Sciences,* 16th ed., Mack Publishing Company, Easton, Pa. (1980), page 1245 and pages 1576-1582.

The shell of the present capsule comprises about 20-45%, preferably 23-41%, and most preferably about 28-36% of gelatin. The gelatin may be of Type A, Type B, or a mixture thereof. Bloom numbers, the indicator of gelatin strength, may range from about 60-300.

The starting gelatin material of the present capsule is modified to produce "soft gelatin" by the addition of a plasticizer to the gelatin. The addition of plasticizer is necessary in order to achieve the softness and flexibility of the capsule shell required for chewability. Useful plasticizers of the present invention include glycerin (1,2,3-propanetriol), D-sorbitol (D-glucitol), or similar low molecular weight polyols. Glycerin and D-sorbitol may be obtained from the Sigma Chemical Company, St. Louis, Mo. The shell of the present capsule comprises about 17.5-35%, preferably 19-31%, and most preferably about 22-28% of plasticizer. The preferred plasticizer of the present invention is glycerin.

Water

The shell of the present soft gelatin capsule comprises about 15-30%, preferably about 17-29%, and most preferably about 20-26% of water. The water content of the shell aids in its rapid dissolution upon contact with saliva and other gastric fluids present in the mouth.

The amount of water contained in the present capsule shell is in contrast with the higher water content employed in Krueger (U.S. Pat. No. 2,580,683), which discloses capsule shells of gelatin, sugar and a minimum of about 34% water. A shell composition of about 45% water is also disclosed by Krueger. Similarly, Morishita (Japanese Application No. 56-89833) discloses a capsule shell comprising about 44% water.

Hydrogenated Starch Hydrolysate

In order to augment the taste and chewability of the capsule shell, as well as to assist in the rapid dissolution of the shell upon chewing, the present capsule shell further comprises a hydrogenated starch hydrolysate.

Hydrogenated starch hydrolysates useful in the present shell include those which contain less than 3% of polyols whose degree of polymerization (DP) is higher than 20, about 35-60% of maltitol (DP 2), about 0.1-20% of sorbitol (DP 1), and the balance being constituted by a mixture of polyols of DP 3 to 20. Preferably, the hydrolysates are characterized by a content of lower than 1.5% of polyols whose DP is higher than 20, 5-8% of sorbitol, 50-53% of maltitol, and the balance being constituted by a mixture of polyols of DP 3 to 20. The raw starch material selected for hydrolysis may be any type of starch; for example, potato starch, manioc starch, wheat starch, and the like may be utilized.

The hydrogenated starch hydrolysates useful in the present shell are prepared by a two-step method. First, a starch "prehydrolysate" of dextrose (D-glucose) equivalent of 10-35 is subjected to partial hydrolysis which is enzymatically catalyzed by at least the action of a $\beta$-amylase. Hydrolysis is continued until the dextrose equivalent of the resulting starch hydrolysate is brought to a value of 45-53. When the original prehydrolysate has a dextrose equivalent of 10-27, the supplementary enzymatic action of $\alpha$-amylase is also included in the hydrolysis step. At the completion of the hydrolysis step, the starch hydrolysate is in the form of a syrup which comprises D-glucose (dextrose), disaccharides, tri- to hexasaccharides, for example, maltose and sucrose, and saccharides higher than hexasaccharides.

In a second preparation step, the starch hydrolysate is hydrogenated in order to produce sugar alcohols. The hydrogenation is continued until a reducing sugar content of less than about 0.2%, and preferably less than about 0.1%, is attained by the Raney nickel method, i.e., by high pressure hydrogenation similar to glucose hydrogenation. The hydrolysate is introduced into a hydrogenation reactor after purification with activated carbon and resins and following concentration until a dry matter content of about 37-40%. The hydrogenation takes place in the presence of a Raney nickel catalyst, at a temperature of about 100°-150° C. and under a hydrogen pressure of about 40-70 kg/cm$^2$, and is brought to a close after a reaction time of about 2-4 hours. The catalytic agent constituted by the Raney nickel is separated from the hydrogenated hydrolysate by decantation. Successively, the hydrogenated hydrolysate is introduced into a conical decanting device, filtered in order to remove the ultimate traces of catalytic agent, demineralized on cationic and anionic resins, and evaporated until the desired dry matter content is obtained. At the completion of these steps, the finished product is in the form of a colorless, odorless, clear syrup with a pleasant sweet taste and no aftertaste. The hydrogenated starch hydrolysate is non-cariogenic (i.e., does not cause tooth decay), and is of high organic and mineral purity. Its viscosity is about 1500-2100 centipoises, measured at 20° C. with a concentration of about 74% dry matter.

One commercially-available hydrogenated starch hydrolysate comprises the following, on a dry basis:

about 0–3% hydrogenated saccharides with degree of polymerization greater than 20; about 6–8% D-sorbitol (D-glucitol), the sugar alcohol produced by the hydrogenation of glucose in the starch hydrolysate; about 50–55% hydrogenated disaccharides, primarily maltitol, the sugar alcohol produced by the hydrogenation of maltose; and the balance being constituted by a mixture of polyols of DP 3 to 20. Based on this carbohydrate profile, the average molecular weight of this product is about 630. Its pH in solution is from about 5 to 7. The refractive index is from about 1.4760–1.4830.

A hydrogenated starch hydrolysate is present in the shell of the present soft gelatin capsule in a weight percentage of about 5–25%, and preferably from about 18–22%. It has been discovered that the presence in the capsule shell of the hydrogenated starch hydrolysate in these amounts augments the chewable and palatable properties of the shell, as well as assists in its rapid dissolution upon chewing. Unlike the soft gelatin capsule disclosed by Ebert et al. (U.S. Pat. No. 4,428,927), in which the presence of a natural or synthetic masticatory substance in the capsule shell insures that an insoluble residue is left in the mouth which does not change significantly in size upon continued chewing, the presence of the hydrogenated starch hydrolysate in the present capsule shell ensures that the shell will quickly dissolve as it is chewed. This quick-dissolving property makes the present capsule particularly effective for administration of medicines or other biologically-active substances to persons in medical distress, to the elderly, to children, or to animals, all of whom may not be able to swallow a hard capsule or to chew a soft capsule for a prolonged period. In addition, the pleasant, sweet taste imparted by the hydrogenated starch hydrolysate makes the present capsule more palatable than capsules which are tasteless or unpleasant-tasting.

Soft Gelatin Capsule Fill Material

The present soft gelatin capsule shell will enclose a preselected quantity of fill material. Preferably, this enclosed fill material will constitute a pharmaceutical unit dosage of a biologically-active substance such as a drug, mineral, or vitamin. The fill material of the present capsule can take one of several forms: (i) liquid; (ii) semi-solid; (iii) solid; or (iv) gel. In all cases, the fill material of the present capsule will contain about 5–7% or less water so that deterioration of the aqueous shell is minimized.

In the liquid form of the present capsule fill material, one or more biologically-active compounds can be dispersed or dissolved in a non-toxic liquid base. Preferably the liquid base of the present capsule fill material is a vegetable oil. Suitable vegetable oils for use in the present capsule fill material include corn oil, peanut oil, safflower oil, sunflower oil, and soybean oil. The liquid base may also comprise a liquid polyalkylene glycol. For example, a mixture of polyalkylene glycols having a mean molecular weight of 200–4000, and lower alcohols having 2–8 carbon atoms and 1–3 hydroxy groups, is disclosed by Bossert et al. (U.S. Pat. No. 3,784,684). When this mixture is employed as a carrier for a measured amount of 4-(2'-nitrophenyl)-2,6-dimethyl-3,5-dicarbomethoxy-1,4-dihydropyridine, a known coronary dilator, and is encapsulated in a soft gelatin capsule shell, an instant oral-release capsule is provided for treatment of angina pectoris. Mixed with the liquid solvent base of the present capsule may optionally be non-aqueous sweeteners such as sodium saccharin; and non-aqueous flavorings such as cinnamon or cinnamon oil, citric acid, lemon oil, nutmeg oil, orange oil, peppermint oil, rose oil, spearmint or spearmint oil, and strawberry oil.

The present soft gelatin capsule may also encapsulate a solid fill material. Useful solid fill materials include tablets or pellets comprising an active ingredient which can be further coated with gelatin, sugar, and the like, as disclosed by Glassman (U.S. Pat. No. 3,228,789).

A semi-solid fill material may also be encapsulated by the present soft gelatin capsules. The biologically-active agent may be dispersed in a substantially water-free carrier mixture comprising in major proportion one or more polyalkylene glycols, preferably comprising a mixture of a major proportion of a liquid polyethylene glycol and a minor proportion of a waxy polyethylene glycol; and in minor proportion a $C_2$–$C_4$ diol or triol, preferably propylene glycol. As disclosed by Shah et al. (U.S. Pat. No. 4,486,412), the active agent dispersed in the mixture is preferably one or more basic salts, such as a magnesium, aluminum, or calcium salt which acts as an antacid to neutralize stomach acid. Flatulence relieving agents which are compatible with the basic salts may also be included. Suitable flavorings and sweeteners may also be added to the semi-solid fill material of the present capsule to ensure the palatability of the fill.

The present soft gelatin capsules may also enclose a gel fill comprising a gelled polymeric matrix. As disclosed by Cohen et al. (U.S. Pat. No. 4,708,834), a polymeric matrix may be formed by gelation of a liquid fill, following its encapsulation in a gelatin capsule shell. The gelled fill may comprise a solution or dispersion of an active ingredient in a polysaccharide gum, such as a vegetable gum. The gellable fill may also include optional amounts of cosolvents, buffers, surfactants, thickeners, sweeteners, flavorings, and the like.

All of the fill materials discussed above may incorporate one or more pharmaceutically-active compounds which will be present in the fills, in amounts which may vary widely depending upon the biological activity, and the solubility of the active compound(s). Useful classes of pharmaceutically-active compounds which may be delivered by the present capsules include analgesics, calcium channel blockers, beta-blockers, antibacterials, antidepressants, antidiabetics, anti-inflammatory agents, cerebral stimulants, sedatives, anti-parasitics, decongestants, muscle relaxants, anti-Parkinsonism agents, bronchodilators, and nutritional supplements such as vitamins, minerals, fatty acids, and the like.

The invention will be further described by reference to the following detailed examples.

EXAMPLE I

VITAMIN C AND IRON DOSAGE FORM

A soft gelatin capsule fill composition is prepared which comprises the following:

| Ingredient | Amount | Weight Percent |
| --- | --- | --- |
| Ascorbic Acid | 30 parts | 6.0 |
| Iron Salts | 38 parts | 7.6 |
| Sodium Saccharin | 1 part | 0.2 |
| Orange Flavoring | 3 parts | 0.6 |
| Citric Acid | 4 parts | 0.8 |
| Vegetable Oil | 423 parts | 84.8 |

1. Fill Preparation

The vegetable oil is mixed with the orange flavoring, sodium saccharin, and citric acid in a suitable vessel until a uniform mixture results. Ascorbic acid and iron salts are subsequently added and agitation is continued for about 45 minutes. The resulting semi-liquid blend is then milled and degassed.

2. Shell Preparation

A soft gelatin shell is prepared which comprises the following:

| Ingredient | Amount | Weight Percent |
| --- | --- | --- |
| Gelatin | 32 parts | 32 |
| Glycerin | 25 parts | 25 |
| Water | 23 parts | 23 |
| Hydrogenated starch hydrolysate | 20 parts | 20 |

The gelatin, glycerin, water, and hydrogenated starch hydrolysate are added to a suitable vessel and agitated, subsequently with heat, until a uniform melt results.

3 Encapsulation

The soft gelatin shell preparation above is employed to encapsulate 500 mg portions of the semi-liquid fill composition employing standard encapsulation technology (#9 round die) to produce one-piece, hermetically sealed soft gelatin capsules.

EXAMPLE II

CALCIUM DOSAGE FORM

1. Fill Preparation

A soft gelatin capsule fill composition is prepared which comprises the following:

| Ingredient | Amount | Weight Percent |
| --- | --- | --- |
| Calcium Carbonate | 750 parts | 40.0 |
| Sodium Saccharin | 1 part | 0.05 |
| Strawberry Flavoring | 13 parts | 0.7 |
| Citric Acid | 6 parts | 0.3 |
| Vegetable Oil | 1100 parts | 59.0 |

The vegetable oil is mixed with the strawberry flavoring, sodium saccharin, and citric acid in a suitable vessel until a uniform mixture results. Calcium carbonate is subsequently added and agitation is continued for about 45 minutes. The resulting semi-liquid blend is then milled and degassed.

2. Shell Preparation

A soft gelatin shell is prepared which comprises the following:

| Ingredient | Amount | Weight Percent |
| --- | --- | --- |
| Gelatin | 32 parts | 32 |
| Glycerin | 25 parts | 25 |
| Water | 23 parts | 23 |
| Hydrogenated starch hydrolysate | 20 parts | 20 |

The gelatin, glycerin, water and hydrogenated starch hydrolysate are added to a suitable vessel and agitated, subsequently with heat, until a uniform melt results.

3. Encapsulation

The shell preparation above is employed to encapsulate 1870 mg portions of the semi-liquid fill composition employing standard encapsulation technology (#20 round die) to produce one-piece, hermetically sealed soft gelatin capsules.

When ingested and chewed, the capsules of Examples I and II readily rupture to release their contents in the mouth of the user. The capsule shell quickly dissolves so that it can be swallowed along with the capsule fill material. No sticky or gummy residue remains in the mouth of the user after a few seconds of chewing. Both the shell and the fill yield a pleasant taste and mouthfeel when ingested in this manner.

While certain representative embodiments of the invention have been described herein for purposes of illustration, it will be apparent to those skilled in the art that modifications therein may be made without departing from the spirit and scope of the invention.

What is claimed is:

1. A chewable, edible soft gelatin capsule which comprises:
   (a) a soft gelatin shell which comprises:
      about 20–45% gelatin;
      about 15–30% water;
      about 17.5–35% plasticizer; and
      about 5–25% hydrogenated starch hydrolysate;
      and wherein said shell encloses
   (b) a soft gelatin capsule fill material.

2. The capsule of claim 1 wherein said plasticizer is comprised of glycerin or sorbitol or a mixture thereof.

3. The capsule of claim 1 wherein said plasticizer is comprised of glycerin.

4. The capsule of claim 1 wherein said fill material provides a pharmaceutical unit dosage form of a biologically-active substance.

5. The capsule of claim 4 wherein said biologically-active substance comprises vitamins, minerals, or a mixture thereof.

6. The capsule of claim 4 wherein said biologically-active substance is an antacid.

7. The capsule of claim 1 wherein said fill material is a liquid.

8. The capsule of claim 7 wherein said fill material comprises a vegetable oil.

9. The capsule of claim 7 wherein said fill material comprises a liquid polyalkylene glycol.

10. The capsule of claim 1 wherein said fill material is a solid.

11. The capsule of claim 10 wherein said fill material comprises solid tablets or pellets.

12. The capsule of claim 1 wherein said fill material is a semi-solid.

13. The capsule of claim 12 wherein said semi-solid comprises a dispersion of a biologically-active agent in a mixture comprising in major proportion a polyalkylene glycol and in minor proportion a $C_2$–$C_4$ diol or triol.

14. The capsule of claim 1 wherein said fill material comprises a gel.

15. The capsule of claim 14 wherein the fill comprises an active ingredient dispersed throughout a gelled polysaccharide matrix.

16. The capsule of claim 1 wherein the hydrogenated starch hydrolysate comprises about 35–60% hydrogenated disaccharides.

17. The capsule of claim 16 wherein the disaccharides comprise a major portion of maltitol.

18. The capsule of claim 16 wherein the hydrogenated starch hydrolysate comprises about 0.1–20% sorbitol.

19. The capsule of claim 16 wherein the hydrogenated starch hydrolysate comprises about 35–60% maltitol.

* * * * *